United States Patent
Dottori et al.

(10) Patent No.: US 9,434,961 B2
(45) Date of Patent: Sep. 6, 2016

(54) CONTINUOUS PROCESS FOR THE PRODUCTION OF ETHANOL FROM LIGNOCELLULOSIC BIOMASS

(75) Inventors: Frank A. Dottori, Temiscaming (CA); Robert Ashley Cooper Benson, North Bay (CA); Régis-Olivier Benech, Chatham (CA); Richard Romeo Lehoux, Windsor (CA); Christopher Bruce Bradt, LaSalle (CA)

(73) Assignee: GREENFIELD SPECIALTY ALCOHOLS INC., Toronto (CA)

( * ) Notice: Subject to any disclaimer, the term of this patent is extended or adjusted under 35 U.S.C. 154(b) by 0 days.

(21) Appl. No.: 13/291,659

(22) Filed: Nov. 8, 2011

(65) Prior Publication Data

US 2012/0115200 A1    May 10, 2012

Related U.S. Application Data

(60) Provisional application No. 61/411,858, filed on Nov. 9, 2010.

(51) Int. Cl.
*C12P 7/10* (2006.01)

(52) U.S. Cl.
CPC . *C12P 7/10* (2013.01); *Y02E 50/16* (2013.01)

(58) Field of Classification Search
None
See application file for complete search history.

(56) References Cited

U.S. PATENT DOCUMENTS

2008/0057555 A1* 3/2008 Nguyen ........................ 435/165

FOREIGN PATENT DOCUMENTS

| CN | 101235392 | 8/2008 |
| CN | 101240297 | 8/2008 |
| WO | WO 2010071805 A2 * | 6/2010 |

OTHER PUBLICATIONS

Converti A et al. Wood hydrolysis and hydrolysate detoxification for subsequent xylitol production. 2000. Chemical Engineering and Technology. 23. p. 1013-1020.*

Rodrigues RCLB et al. In the influence of pH, Temperature, and Hydrolyzate Concentration on the Removal of Volatile and Non-volatile Compounds from Sugarcane Bagasse Hemicellulosic Hydrolyzate Treated with Activated Charcoal Before or After Vacuum Evaporation. 2001. Brazilian Journal of Chemical Engineering. vol. 18 No. 3 p. 1-15.*

Tengborg et al., "Comparison of SO2 and H2SO4 impregnation of softwood prior to steam pretreatment on ethanol production", Applied Biochemistry and Biotechnology, Mar. 1998, vol. 70-72, Issue 1, pp. 3-15.

Eklund et al., "The Influence of SO2 and H2SO4 impregnation of willow prior to steam pretreatment", Bioresource Engineering, Jan. 1995, vol. 52, pp. 225-229.

Lee et al., "Recent developments of key technologies on cellulosic ethanol production", Journal of Scientific & Industrial Research, Nov. 2008, vol. 67, pp. 865-873.

Brethauer et al., "Review: Continuous hydrolysis and fermentation for cellulosic ethanol production", Bioresource Technology, Jul. 2010, vol. 101, pp. 4862-4874.

Hamelinck et al., "Ethanol from lignocellulosic biomass: techno-economic performance in short, middle and long-term", Biomass and Bioenergy, 2005, vol. 28, pp. 384-410.

Cardona et al., "Fuel ethanol production: Process design trends and integration opportunities", Bioresource Technology, Sep. 2007, vol. 98, pp. 2415-2457.

International Patent Application No. PCT/CA2011/050692, International Search Report dated Jan. 25, 2012.

* cited by examiner

*Primary Examiner* — Paul Holland
(74) *Attorney, Agent, or Firm* — Mark F. Vickers; Borden Ladner Gervais LLP

(57) ABSTRACT

A continuous process for the recovery of ethanol from hemicellulose and cellulose from lignocellulosic biomass. Yield of fermentable sugars can be maximized by continuous operation of the pre-treatment system and careful selection of pretreatment conditions including the addition of only small amounts of dilute mineral acid and low pressure. With this approach, the xylose component that is mainly present in its unfermentable oligomeric form in known pre-hydrolysis Kraft processes can be recovered more efficiently and as a monomer that can be fermented by xylose fermenting yeasts and bacteria. Due to the use of only dilute acids, there is a very low loss of glucose and xylose hence very low production of toxic chemicals (e.g. HMF, furfural) in the pretreatment step. The resulting overall fermentation efficiency of both hexose and pentose sugars is 90% of the theoretical maximum.

27 Claims, 3 Drawing Sheets

CONTINUOUS PROCESS FOR THE PRODUCTION OF ETHANOL FROM LIGNOCELLULOSIC BIOMASS

CROSS REFERENCE TO RELATED APPLICATIONS

This application claims the benefit of priority of U.S. Provisional Patent Application No. 61/411,858 filed Nov. 9, 2010, the contents of which is incorporated herein by reference.

FIELD OF THE INVENTION

The present invention generally relates to the production of ethanol from biomass and in particular to a continuous process for the recovery of ethanol from hemicellulose and cellulose from lignocellulosic biomass.

BACKGROUND OF THE INVENTION

World energy consumption is predicted to increase 54% between 2001 and 2025. Considerable research effort is being directed towards the development of sustainable and carbon neutral energy sources to meet future needs.

Biofuels are an attractive alternative to current petroleum-based fuels, as they can be utilized in transportation with little change to current technologies and have significant potential to improve sustainability and reduce greenhouse gas emissions.

Biofuels include fuel ethanol. Fuel ethanol is produced from biomass by converting starch or other carbohydrates to sugars, fermenting the sugars to ethanol, and then distilling and dehydrating the ethanol to create a high-octane fuel that can substitute in whole or in part for gasoline.

In North America, the feedstock for the production of fuel ethanol is primarily corn, while in Brazil sugar cane is used. There are disadvantages to using potential food or feed plants to produce fuel. Moreover, the availability of such feedstocks is limited by the overall available area of suitable agricultural land. Therefore, efforts are being made to generate ethanol from non-food sources, such as cellulose, and from crops that do not require prime agricultural land.

One such non-food source is lignocellulosic biomass. Lignocellulosic biomass may be classified into four main categories: (1) wood residues (sawdust, bark or other), (2) municipal paper waste, (3) agricultural residues (including corn stover, corncobs and sugarcane bagasse), and (4) dedicated energy crops (which are mostly composed of fast growing tall, woody grasses such as switchgrass and miscanthus).

Lignocellulosic biomass is composed of three primary polymers that make up plant cell walls: Cellulose, hemicellulose, and lignin. Cellulose fibres are locked into a rigid structure of hemicellulose and lignin. Lignin and hemicelluloses form chemically linked complexes that bind water soluble hemicelluloses into a three dimensional array, cemented together by lignin. Lignin covers the cellulose microfibrils and protects them from enzymatic and chemical degradation. These polymers provide plant cell walls with strength and resistance to degradation, which makes lignocellulosic biomass a challenge to use as substrate for biofuel production.

There are two main approaches to the production of fuel ethanol from biomass: thermochemical and biochemical. Thermochemical processes convert the biomass to a reactive gas called syngas. Syngas is converted at high temperature and pressure to ethanol by a series of catalyzed processes. Biochemical processes use biocatalysts called enzymes to convert the cellulose and hemicellulose content to sugars, which are then fermented to ethanol and other fuels such as butanol.

Biochemical conversion of lignocellulosic biomass to ethanol in general involves five basic steps (1) Feed preparation—the target biomass is cleaned and adjusted for size and moisture content; (2) Pretreatment—exposure of the raw biomass to high pressure and temperature for a specified duration; with or without catalyzing additives; (3) Hydrolysis—conversion of the pretreated biomass to simple sugars using special enzyme preparations to hydrolyze pretreated plant cell-wall polysaccharides to a mixture of simple sugars; (4) Fermentation, mediated by bacteria or yeast, to convert these sugars to fuel such as ethanol; and (5) Distillation and Dehydration of the ethanol/fuel.

Efforts to ferment glucose (derived from cellulose) and xylose (derived from hemicellulose) simultaneously have been largely unsuccessful. The fermentation of the glucose component is easily carried out even in the harsh conditions following pretreatment and hydrolysis, however the fermentation of xylose has not been demonstrated on a commercial scale. Yeasts exist that will ferment xylose in pure sugar streams but they are ineffective in fermenting xylose in hydrolysates produced from lignocellulosic biomass, due to their sensitivity to inhibitory compounds in the hydrolysate.

In known pre-hydrolysis kraft dissolving pulp production process, the biomass wood chips are pre-treated in a batch pre-hydrolysis to remove hemicellulose. Water and chemical intensive batch washing systems, low recovery yield of soluble hemicellulose sugars and recovery of hemicellulose sugars primarily in oligomeric hence unfermentable form are the main defects of these processes.

Thus, compared to the prior art processes, a more economical and effective approach for dealing with the problem of xylo-oligomers and inhibitory compounds produced during pretreatment, is desirable.

SUMMARY OF THE INVENTION

It is now an object of the present invention to provide a process which maximizes the extraction yield of glucose and xylose from the feedstock.

It is a further object of the invention to provide a lignocellulosic biomass process wherein both the glucose and xylose components of the biomass are fermented to make ethanol.

The inventors of the present continuous process have surprisingly discovered that the combination of several distinct continuous unit operations in an unconventional manner allows the economical production of ethanol from lignocellulosic biomass.

The use of strong acids, such as mineral acids, during pretreatment is known. However, the inventors have now surprisingly found that the yield of fermentable sugars can be maximized by careful selection of continuous pretreatment conditions including the addition of only small amounts of dilute mineral acid. With this approach, the xylose component that is often present in its unfermentable oligomeric form can be recovered as a monomer that can be fermented by xylose fermenting yeasts. Due to the use of only dilute acids, there is a very low loss of glucose in the pretreatment step. The resulting overall fermentation efficiency of both hexose and pentose sugars is up to 90% of the theoretical maximum. A further advantage of the new process is the integration of steam and energy between the process steps.

BRIEF DESCRIPTION OF THE DRAWINGS

Other objects and advantages of the invention will become apparent upon reading the detailed description and upon referring to the drawings in which.

DETAILED DESCRIPTION OF PREFERRED EMBODIMENTS

Before explaining the present invention in detail, it is to be understood that the invention is not limited to the preferred embodiments contained herein. The invention is capable of other embodiments and of being practiced or carried out in a variety of ways. It is to be understood that the phraseology and terminology employed herein are for the purpose of description and not of limitation.

Throughout this description any reference to washing or extracting steps is intended to encompass any process for the mechanical separation of liquids from solids and draining of the liquid, with or without the addition of water or solvents, including but not limited to aqueous extraction, solvent extraction, filtering, centrifuging, pressing, venting, draining, purging or the like with or without the addition of eluents.

Processes are known that convert lignocellulosic biomass by biochemical conversion into biofuels. These processes have several defects. Typically, the valuable hemicellulose component is degraded to volatile impurities of little value. These processes also fail to convert the xylose component of hemicellulose to ethanol in an economical way because the xylose stream includes acetic acid and other volatile impurities that inhibit the fermentation by specialized xylose fermenting yeasts. In existing processes the hydrolysis step is impeded by the presence of hemicellulose and other inhibitors.

The present continuous process overcomes at least some of the above difficulties through the following key steps.

Figure 1:
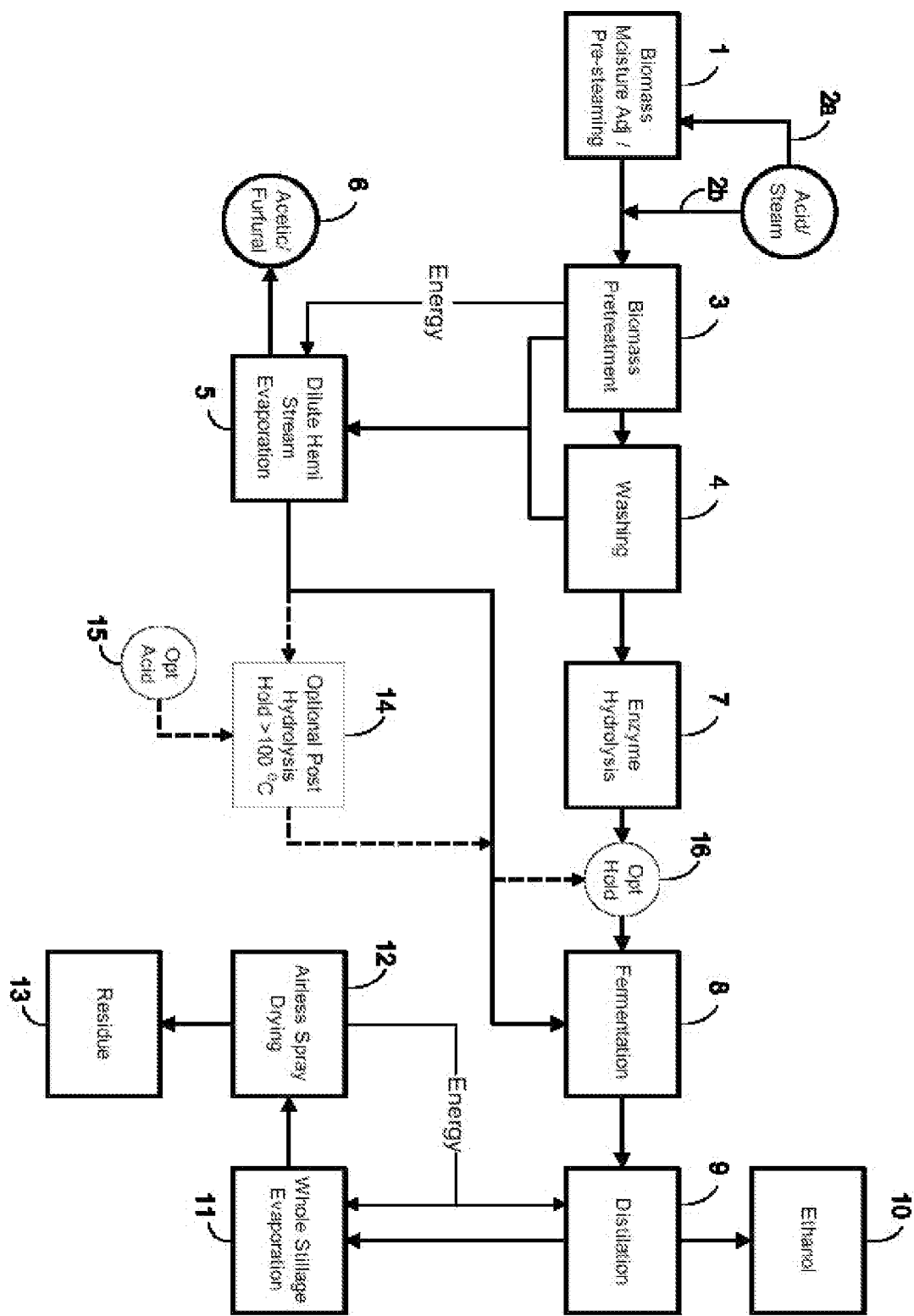
FIG. 1 is a general schematic overview of the continuous process.

With reference to FIG. 1, the moisture content of the biomass is controlled (Step 1) by a combination of pre-steaming and water addition to achieve a specific moisture content.

A continuous steam explosion pretreatment is carried out (Step 3) using a small amount of mineral acid at low pressure and temperature, thereby producing a high yield of monomeric xylose and purified cellulose polymer. By keeping the acid content at a level below 1% (w/w on incoming biomass dry matter basis), the normally needed exotic and expensive metallurgy in the steam pretreatment system can be avoided.

The steam explosion pretreatment system is discussed as follows. In the continuous process, pressurized activated cellulose is flashed into a cyclone by rapidly releasing the pressure to ensure an explosive decompression of the pre-treated biomass into fibrous solids and vapors. This opens up the fibres to increase accessibility for the enzymes. Purified cellulose with a low level of residual hemicellulose can be sent to the hydrolysis and fermentation stages.

The recovery of both cellulose and hemicellulose is maximized by carefully choosing pH, temperature, and retention time of the exposing step. Best recovery is obtained by carefully adapting operating conditions (e.g. pre-treatment pressure, temperature, time and pH value) based on feedstock used.

The biomass is preferably chopped or ground and pre-heated with live steam at atmospheric pressure prior to being fed into the continuous pretreatment system. Air is removed from the incoming biomass by pressing. Liquefied inhibiting extracts can be removed at this time. Acid is added, if required, to lower the pH to the desired value for catalyzing the breakdown/hydrolysis of the hemicellulose and activating the cellulose fraction during the cooking step. Pressed impregnated biomass is then cooked with steam at elevated temperatures and pressures for a preselected amount of time.

A sufficient residence time is provided to ensure proper breakdown/hydrolysis of the hemicellulose and activation of the cellulose fraction. During pretreatment, the purging of condensate and venting of volatiles occurs continuously.

The pretreated biomass is liquid extracted while under pressure and prior to exiting the pretreatment reactor or after exiting or both. Minimal water is used as an eluent to remove water soluble or water emulsified hemicellulose and cellulose hydrolysis and degradation products, primarily xylose, but also acetic acid and xylo-oligosaccharides, and to a lesser extent furans, fatty acids, sterols, ester, and ethers.

Extraction refers in general to a single or multiple step process of removing liquid portions from the fibers with or without addition or utilization of an eluent, (the diluting step). Typically the extraction is enhanced by use of a mechanical compressing device such as a modular screw device. The eluent can be recycled to increase the economy of its use or used for example in the known process of counter current washing. Soluble and suspended or emulsified components in the steam treated lignocellulosic biomass are removed from the fibrous solids. The subsequent eluent wash water, which contains hemicellulose products that are inhibitory to downstream hydrolysis and fermentation steps, is sent to a recovery step.

The extracting system generally uses a device that employs mechanical pressing or other means to separate solids from liquid. This can be accomplished under pressure as described above and/or at atmospheric pressure with different types of machines, the details of which are not essential to this invention.

The extract stream containing the soluble fraction of hemicellulose is continuously collected and concentrated to the desired dryness for further applications. A final refining step is required for producing xylose and xylo-oligosaccharides with a degree of purity suitable for pharmaceuticals, food and feed, and agricultural applications. Vacuum evaporation can be applied in order to increase the concentration and simultaneously remove volatile compounds such as acetic acid and flavors or their precursors. Solvent extraction, adsorption and ion-exchange precipitation have been proposed by those skilled in the art.

A balance must be maintained between the removal of the water soluble components (primarily xylose monomers with remaining xylo-oligosaccharide fraction) and the need to minimize the amount of washing/eluent water added. It is desirable to minimize water use, as xylose monomers and xylo-oligosaccharide fraction must eventually be concentrated.

During the steam explosion pretreatment, liquids and gases are continuously vented to remove impurities and to recover dissolved sugars. This system has been described above. Continuous steam explosion pretreatment is arranged to maximize the recovery of dissolved xylose monomers and also to maximize the digestibility of the purified cellulose stream by enzymes.

The pre-treatment is arranged to maximize recovery of xylose in a fermentable monomeric form by (i) adjusting the moisture content of the incoming biomass to 50%-80%, preferably 65%-75%, most preferably 70%; (ii) carrying out the continuous pre-treatment under mild temperature and pressure conditions that depend on the feedstock used, for instance, (1) temperature of 160° C. and pressure of 110 psig for hardwood such as aspen/poplar wood (2) temperature of 140° C. to 160° C. and pressure of 35 psig to 75 psig preferably 150° C. and 55 psig for agricultural residues such as corncob, ; and (iii) in the presence of low concentration of mineral acid (i.e. 0.5% to 0.9%, preferably 0.7% to 0.9%, most preferably 0.8% w/w on incoming biomass dry matter basis); (iv) purging continuously solubilised xylose as it is formed; and (iv) venting continuously the pre-treatment vessel to reduce degradation reactions.

The pre-treatment is also arranged to maximize the digestibility of the purified cellulose stream by enzymes by (i) carefully selecting pre-treatment temperature, pressure, time and pH conditions based on feedstock used i.e. temperature and pressure (e.g. for agricultural residues, temperature of 140° C. to 160° C. and pressure of 35 psig to 75 psig preferably 150° C. and 55 psig), Time (i.e. 60 min to 180 min, preferably 90 min to 150 min, most preferably 120 min) and, pH value (i.e. pH 1.0 to pH 3.0, preferably pH 1.5 to pH 2.3, most preferably pH 2.0) and, (ii) solubilising, purging and venting inhibitors e.g. hemicellulose sugars, organic acids and furans.

After pretreatment, the prehydrolysed biomass exiting the continuous system is carefully washed to recover a hemicellulose stream that is rich in xylose monomers along with partially solubilized cellulose and to produce a cellulose stream that contains only about 4% to 8% 12% xylose, preferably 8% to 10%, most preferably 8%.

Extraction of the soluble hemicellulose sugars from the wet fraction of the prehydrolysed biomass is carried out by squeezing of the treated fibers with/or without eluent addition under pressure. The hemicellulose stream is high in acetic acid and other volatile impurities that prevent it from being fermented by xylose fermenting yeast. These yeasts are known to be very sensitive to impurities created or released during pretreatment.

After extraction of the soluble hemicellulose sugars from the prehydrolysed biomass (Step 4), this stream of hemicellulose sugars is combined with the stream of soluble hemicellulose purged during pre-treatment (Step 3) to form the hemicellulose rich stream. In order to reduce the impurities in the xylose rich stream, the stream is concentrated by evaporation in Step 5 to evaporate and thereby remove the volatile impurities, primarily furfural, formic acid and acetic acid.

Concentration of the hemicellulose rich stream can be carried out either at atmospheric pressure (i.e. 90° C.-100° C., preferably 98° C.); under vacuum (i.e. 70° C.-85° C., 50 to 250 mbar, preferably 80° C. and 150 mbar); or under pressure (i.e. 5 psig to 35 psig, preferably 20 psig).

The xylose rich stream is concentrated to reach the desired concentration of xylose monomers i.e. 100 gpl to 150 gpl, preferably 110 gpl to 140 gpl, most preferably 120 gpl.

The resulting concentrated xylose rich stream also contains soluble cellulose polymers and some remaning short chain xylo-oligosaccharides. In order to hydrolyze these polymers to glucose, and xylose the concentrate may be held at temperatures at or above 100° C., with or without the addition of sulfuric acid (step 14, 16). The concentrated, evaporated xylose rich stream is then combined with the hydrolysate exiting the enzymatic hydrolysis process prior to fermentation (step 7). By combining the concentrated xylose stream with the glucose rich hydrolysate stream that is low in impurities, the average concentration of sugars is maintained while the content of acetic acid is diminished to a level below 3 gpl. The two sugar streams may then be fermented using commercially available yeasts to obtain an improved yield of ethanol from the biomass.

Energy requirements for the hemicellulose evaporation step are minimized by using the steam from the pretreatment step in the evaporator.

A standard distillation system has been provided, however the inventors have also provided a method to increase the value of the residual solids from the distillation step. The solid slurry from distillation is evaporated and dried in an airless spray dryer. The dry powder may be used as a fuel in a biomass burning boiler or as a raw material for chemical end uses.

Evaporated water from the exit of the airless spray dryer joins with the superheated steam used as the drying medium. The combined steam is used to provide process heat for other unit operations such as separation and distillation of the alcohol in the fermented beer.

The references in the following description of Steps 1 to 15 refer to FIG. 1.

Step 1 & 2: Pre-Steaming, Squeezing, Biomass Impregnation and Moisture Adjustment The biomass is sized and steamed at atmospheric pressure in a bin for 10-60 min. The material is then transferred to a squeezing device where the steamed biomass is compressed up to 6-1 preferably 3-1 and a liquid stream is removed. Then acid catalyst and water are added to achieve desired pH value and moisture content. The acid and water get evenly distributed as the squeezed biomass acts like a sponge and takes on the catalyst much better. Moisture content of the lignocellulosic feedstock with a particle size of 0.5 to 1 cm is adjusted to 50%-80%, preferably 65%-75%, most preferably 70%. Moisture adjustment of the incoming biomass can be carried out by soaking, spraying, steaming or any combination thereof.

Step 2: Biomass Impregnation with Acid Catalyst & Pre-Steaming

The acid catalyst is preferably a mineral acid e.g. sulphuric acid or sulphur dioxide. The acid catalyst is added to the biomass in the amount of 0.5% to 0.9%, preferably 0.7% to 0.9%, most preferably 0.8% w/w on incoming biomass dry matter basis.

The acid catalyst can alternatively be added during Step 1 (biomass moisture adjustment, option 2*a*), right before Step 3 (biomass continuous pre-treatment, option 2*b*) or in both steps.

Acid addition can be carried out by soaking, spraying, steaming or any combination thereof.

The moistened acid-impregnated biomass is pre-steamed for 5 minutes to 90 minutes, preferably 30 minutes to 60 minutes at atmospheric pressure Step 3: Biomass Pre-Treatment After pre-steaming, the moistened acid-impregnated biomass is transferred to the continuous pre-treatment vessel and undergoes pre-treatment under carefully selected conditions that depend on the feedstock used. Continuous pre-treatment is carried out at a temperature of 140° C. to 160° C. and pressure of 35 psig to 110 psig, preferably 110 psig and 160° C. for hardwood and 150° C. for agricultural residues. Pre-treatment temperature and pressure are maintained with direct steam injection. The moistened acid-impregnated biomass is treated for 60 min to 180 min, preferably 45 minutes for hardwood and 90 min to 150 min, most preferably 120 min for agricultural residues at a pH value of pH 1.0 to pH 3.0, preferably pH 1.5 to pH 2.3, most preferably pH 2.0.

During the pretreatment period, soluble components mainly composed of hemicellulose sugar monomers are continuously drained from a low point in the pre-treatment vessel. Volatile components, mainly composed of furans and acetic acid are continuously vented through a vent system at a point above the biomass fill in the pre-treatment vessel.

Step 4: Biomass Washing

The pre-hydrolysate exiting the continuous pre-treatment system is washed by extracting the majority of the soluble components, mainly composed of soluble hemicellulose sugar monomers, remaining in the wet fraction of pre-treated biomass. Extraction of the soluble components is carried out under pressure by squeezing of the treated fibers with/or without eluent addition.

The extracting system in general uses a device that employs a mechanical pressing or other means to separate solids from liquid or air from solids. This is accomplished under pressure and/or at atmospheric pressure with several different types of machines or equipment that vary and the detail of which is not essential to this invention.

After washing, the washed pre-hydrolysate contains 60% to 70% cellulose and 4% to 25% xylose, preferably 6% to 16%, most preferably 8% to 10% by weight on a dry matter basis.

The stream of soluble hemicellulose sugars extracted from the wet fraction of the prehydrolysate (Step 4) is mixed with the stream of soluble hemicellulose sugars drained during pre-treatment (Step 3) to form the hemicellulose rich stream.

Step 5: Hemicellulose Stream Concentration

The hemicellulose rich stream is concentrated to the desired concentration of xylose monomers. Concentration of the hemicellulose stream is carried out by membrane fractionation technologies, solvent extraction, adsorption, ion-exchange precipitation or a combination thereof followed by a step of evaporation. After concentration, the concentration of xylose monomer sugars in the hemicellulose rich stream is 100 gpl to 150 gpl, preferably 110 gpl to 140 gpl, most preferably 120 gpl.

Step 6: Removal of Volatile Compounds from the Hemicellulose Stream

About 80% of the volatile impurities present in solution, primarily furfural, formic acid and acetic acid, are removed during concentration (step 5) and evaporation (step 5 and/or 6) of the hemicellulose stream.

Evaporation of the hemicellulose rich stream is alternatively carried out (i) at atmospheric pressure (i.e. 90° C.-100° C., preferably 98° C.) (ii) under vacuum (i.e. 70° C.-85° C., 50 mbar to 250 mbar, preferably 80° C. and 150 mbar), (iii) under pressure (i.e. 5 psig to 35 psig, preferably 20 psig) or a combination thereof.

After evaporation, the concentration of volatile compounds remaining in solution in is 1 gpl to 6 gpl, preferably 2 gpl to 5 gpl, most preferably 3 gpl.

Step 7: Enzymatic Hydrolysis of the Washed Pre-Hydrolysate

The washed pre-hydrolysate is added to the hydrolysis tank containing water (fresh water or recycled process water), cellulose and hemicellulose degrading enzymes to form a slurry containing 10% to 30% total solids, preferably 15% to 25% total solids, most preferably 17% total solids. Addition of the washed prehydrolysate is carried out over a period of one hour to 60 hours, preferably 10 hours to 25 hours, most preferably 18 hours.

Enzymatic hydrolysis is carried out at 40° C. to 60° C., preferably 45° C. to 55° C., most preferably 50° C.

During hydrolysis, the pH value of the hydrolysate is maintained at pH 4.0 to 6.0, preferably pH 4.5 to pH 5.5, most preferably pH 4.8 to pH 5.2 using alkaline chemicals, preferably aqueous ammonia.

The load of enzyme added is adjusted to reach 60% to 95% of the maximum theoretical cellulose to glucose conversion, preferably 85% to 92%, most preferably 90% in 48 hours to 180 hours, preferably 80 hours to 160 hours, most preferably 120 hours.

Step 8: Co-Fermentation

After hydrolysis, the hydrolysate is combined with the concentrated, evaporated rich xylose stream prior to fermentation. After mixing of both streams, the concentration of fermentable hexose and pentose sugars is 100 gpl to 140 gpl, preferably 110 gpl to 130 gpl, most preferably 125 gpl. Prior to co-fermentation, the mixture contains 55% to 75% hexose and 25% to 45% pentose sugars, preferably 65% hexose and 35% pentose sugars. The mixture also contains 1 gpl to 6 gpl of acetic acid preferably 2 gpl to 4 gpl, most preferably 2 gpl to 3 gpl.

Prior to co-fermentation, the pH is adjusted to pH 5.2 to pH 6.2, preferably pH 5.8 to pH 6.1, most preferably pH 6.0 using alkaline chemicals, and preferably aqueous ammonia.

Co-fermentation is carried out at 28° C. to 36° C., preferably 30° C. to 34° C., most preferably 32° C. using an ethanologenic organism fermenting (i) glucose, most preferably hexose sugars (glucose, galactose, mannose) and xylose, most preferably pentose sugars (xylose, arabinose). The fermenting organism is preferably a fungi, most preferably from the genius *Saccharomyces* and the species *cerevisiae*.

The quantity of fermenting organism added in the fermentation media is adjusted to reach 80% to 95%, preferably 85% to 95%, most preferably 90% to 95% of the maximum theoretical hexose and pentose monomer sugars to ethanol conversion in 24 hours to 90 hours, preferably 36 hours to 72 hours, most preferably 48 hours.

Step 9 &10: Distillation and Ethanol Production

Distillation in general has a few basic steps, but has several embodiments and variations: i) once fermentation has been completed, the "beer", as it is typically called, is sent to a crude separation step where ethanol & water is boiled away from the suspended and dissolved solids of the beer using heat. This is typically called the "Beer Column". It is a distillation column that is run either under vacuum or at atmospheric pressure for producing a vapour or condensed ethanol and water solution free of solids. This then goes to ii) a second column typically called the rectifier which uses heat and a distillation column to separate ethanol and water to its azeotropic maximum approximately 96% v/v ethanol. This then goes to iii) drying, typically done by using a molecular sieve device that uses absorbents, typically activated aluminum oxide pellets, to absorb the remaining water to produce ethanol with less than 1% water for use in fuel.

Step 11: Whole Stillage Evaporation

After distillation has separated the ethanol with water from the solids in the beer the solids, which still contain predominantly water (95% to 80%), are then sent to evaporation typically falling film vacuum driven evaporation that achieves several effects of economy. The solids are typically concentrated to 20% to 60%, and the water evaporated gets treated and recycled back to the process. The condensed whole stillage then goes to spray drying.

Step 12: Airless Spray Drying

The condensed whole stillage is sent to a spray dryer that uses dry super heated steam in a closed system to dry the whole stillage to a fine powder while producing a lower pressure usable steam source for other operations in the plant. Typically the steam produced is sufficient to run the distillation and evaporation steps 9 and 11.

Step 13: Residues Collection

The spray dryer produces a very dry fine powder that is collected and can now be sold as is, upgraded to value added product or sent to a modified boiler to produce steam or electricity or both.

Heat Recovery and Integration

Proper heat recovery and integration is critical for optimizing the commercial value of the process. The pretreatment system energy is captured in the evaporation of the hemi stream and possibly other operations while the heat recovered off the spray drying runs the distillation and evaporation of the whole stillage.

Steps 14, 15 & 16: Optional post-hydrolysis of the xylose rich stream produced in Step 5 and 6 and the C6 rich hydrolysate.

The concentrated xylose rich stream can optionally be held (Step 14) at 100° C. to 140° C., preferably, 110° C. to 130° C., most preferably 120° C. for 60 min to 180 min, preferably 120 min with or without the addition of acid catalyst (Step 15) to complete the conversion of remaining hexose and pentose oligomers to monomers. This optional step of Post hydrolysis can alternatively be carried out prior to or after (Step 16) combining the C5 rich stream with the C6 rich hydrolysate from Step 7.

EXAMPLE

The references in this description refer to FIG. 1. The lignocellulosic feedstock, in this example corncobs chopped to a size of 0.5 to 1 cm, was moistened with acidified water in a rotary mixer to achieve 70% moisture content. This process is not limited to corn cobs. It can be adapted for other feedstocks by carefully adjusting (i) pretreatment temperature, pressure, time, pH value and (ii) load of acid catalyst.

To acidify the water, a quantity of sulfuric acid amounting to 0.8% w/w of the corncobs feed on a dry matter basis was added (Step 2). The acid catalyst can alternatively be added during Step 1 (biomass moisture adjustment, option 2a); or right before Step 3 (biomass pre-treatment, option 2b) or in both steps. The acidified, moistened cobs were conveyed to a batch steam gun in which the corncobs were pre-steamed (Step 1) for 30 minutes at atmospheric pressure. The final moisture content of the corncobs remained 70%. The batch steam gun was then sealed. The pre-steamed, acidified corncobs were then pretreated in the batch steam gun at 150° C. for 120 minutes with directly injected steam. During the pretreatment period, liquid condensate containing soluble corncob components was collected at and drained continuously from a low point in the vessel. Volatile components were continuously removed through a vent system at a point above the biomass fill in the steam gun. At the end of the pretreatment step, the pressure in the steam gun was rapidly released to achieve expolosive decompression of the steam gun contents and the pretreated biomass was discharged to a washing step.

The pretreated corncobs were then diluted with fresh water in a ratio of 10:1 to form a slurry. The slurry was drained and pressed. This step created a solid cake at a moisture content of 50% and a liquid filtrate containing dissolved sugars, acetic acid and other soluble compounds. The solids, containing mainly cellulose and hemicellulose, were shredded in a garden shredder (not shown) and then diluted with fresh water to 17% consistency for hydrolysis and fermentation. The prehydrolysate solids stream obtained was subjected to enzymatic hydrolysis as described further below, to obtain a hydrolyzate stream.

The liquid filtrate, containing xylose and other soluble sugars as well as soluble impurities was subjected to a vacuum (Step 4 to evaporate volatile components). As described above, evaporation of the hemicellulose rich stream is alternatively carried out (i) at atmospheric pressure (i.e. 90° C.-100° C., preferably 98° C.) (ii) under vacuum (i.e. 70° C.-85° C., 50 mbar to 250 mbar, preferably 80° C. and 150 mbar), (iii) under pressure (i.e. 5 psig to 35 psig, preferably 20 psig) or a combination thereof. After evaporation, the concentration of volatile compounds remaining in solution in is 1 gpl to 6 gpl, preferably 2 gpl to 5 gpl, most preferably 3 gpl.

The hemicellulose stream is flashed to atmospheric pressure and obtained as a hot stream. Low grade steam from pre-treatment is sufficient to concentrate the hemicellulose stream on a triple effect evaporator under vacuum conditions to achieve the desired concentrations.

Evaporation was continued until a concentrated hemicellulose solution was obtained with a sugar monomers concentration approximately equal to the glucose concentration in the hydrolyzate stream was achieved. After concentration, the concentration of xylose monomer sugars in the hemicellulose rich stream is 100 gpl to 150 gpl, preferably 110 gpl to 140 gpl, most preferably 120 gpl.

Figure 2:
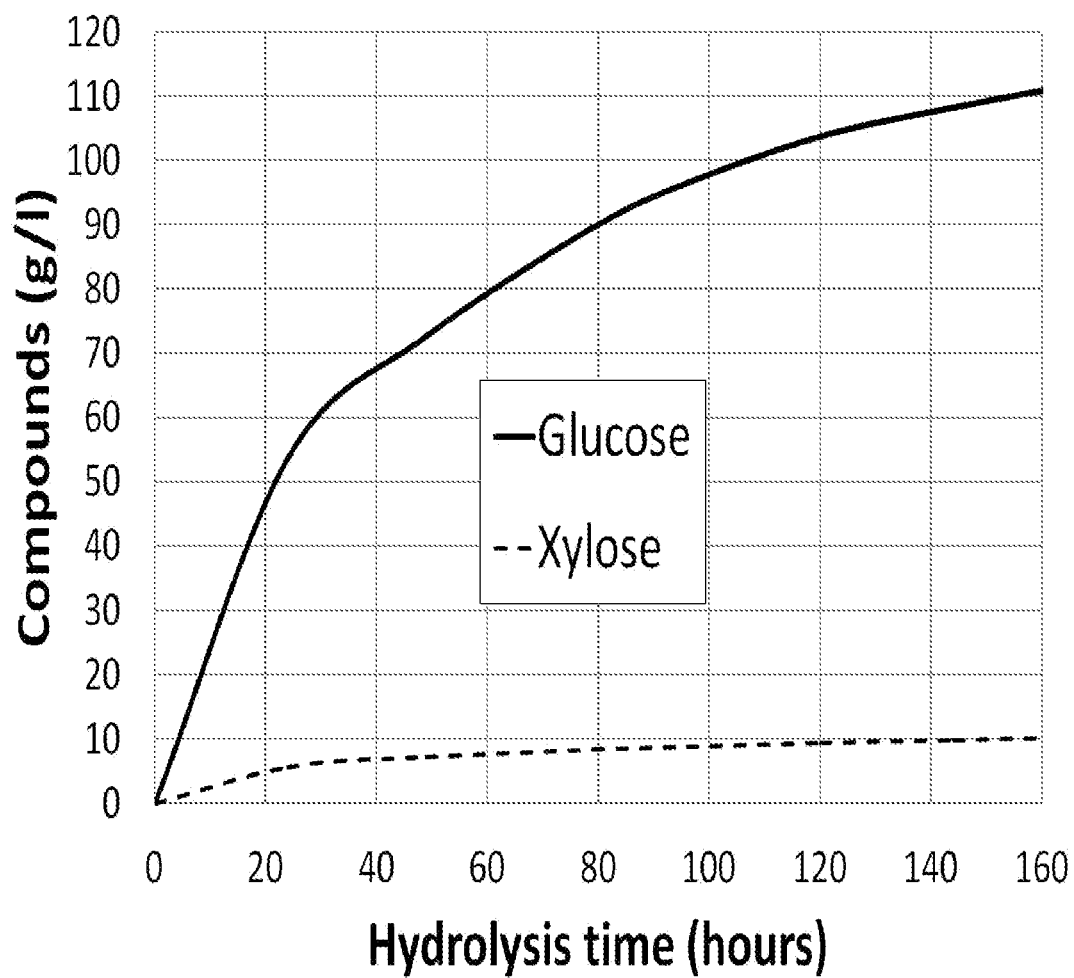
FIG. 2 shows the release of glucose and xylose over the course of enzymatic hydrolysis of biomass pre-hydrolysate.

The prehydrolysate solids stream was hydrolyzed at 50° C., pH 5.0 with a blend of cellulase and hemicellulase enzymes known in the art (FIG. 2). The hydrolysate was then blended with the concentrated hemicellulose solution from Step 4. Fermentation of both glucose and xylose was carried out using yeast able to ferment both hexose and pentose sugars without the addition of nutrients. Cofermentation was carried out at 32° C. Ammonia was added to adjust the initial pH to pH 6.0.

Figure 3:
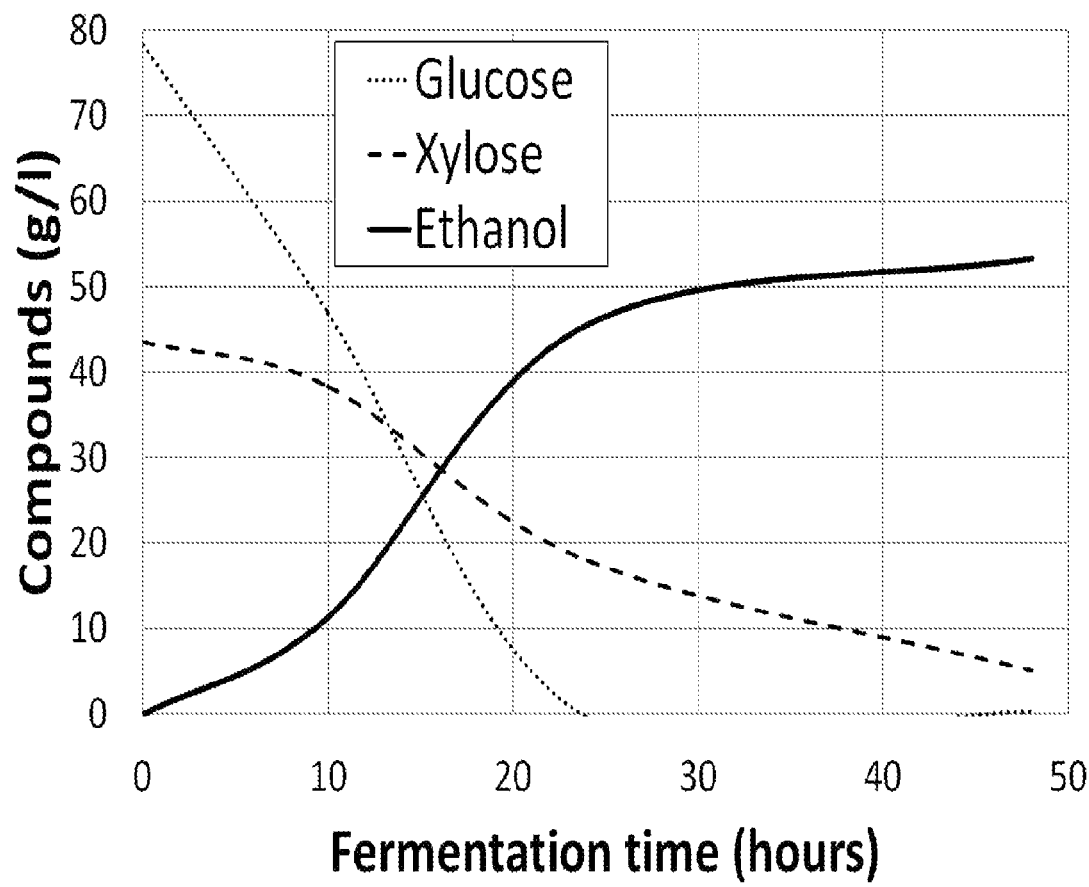
FIG. 3 shows the consumption of xylose and glucose and the production of ethanol from co-fermentation of the hydrolysate and evaporated xylose stream.

The results of the fermentation step are shown in FIG. 3. 90% of the incoming sugar monomers were converted to ethanol within 48 hours. Without adjusting the pH to 6.0, there would none, or extremely slow, conversion of sugars (mainly C5) to ethanol.

Distillation of ethanol can be carried out in a conventional manner.

What is claimed is:

1. A continuous process for converting carbohydrates from lignocellulosic biomass to ethanol, comprising the steps of:
   a) cutting said lignocellulosic biomass to a prescribed size to obtain sized biomass;
   b) steaming said sized biomass from step a) at atmospheric pressure for 10 to 60 minutes to obtain steamed biomass;

c) squeezing said steamed biomass from step b) to remove a first liquid stream and generating squeezed biomass, wherein said steamed biomass is compressed up to 6-1;
d) adding mineral or organic acid to said squeezed biomass from step c) in an amount of 0.5% to 0.9% w/w on an incoming biomass dry matter basis, and pre-steaming said squeezed biomass for 5 to 90 minutes to obtain acidified biomass;
e) adjusting a moisture content of said acidified biomass from step d) to 50% to 80% w/w water, to obtain moisture adjusted acidified biomass;
f) pretreating said moisture adjusted acidified biomass from step e) in a continuous treatment vessel by steam treatment under pressure at a preselected pretreatment temperature for a preselected pretreatment time and at a preselected pretreatment pressure, wherein said preselected temperature is 130° C. to 180° C., said preselected pretreatment time is 30 minutes to 4 hours, said preselected pretreatment pressure is 35-110 psi;
g) continuously purging under pressure from said continuous treatment vessel of step f) volatile components generated by the pressurized steam treatment and liquid condensate formed in the vessel and containing soluble biomass components;
h) submitting to explosive decompression said biomass exiting said continuous treatment vessel of step g) prior to or after the washing step to obtain pre-treated biomass;
i) extracting said pre-treated biomass from step h) with water to recover a cellulose rich solids stream and a liquid stream, wherein said cellulose rich solids stream contains 4% to 8% w/w xylose from remaining xylose, xylooligosaccharides and xylans in said pre-treated biomass;
j) heating the said liquid stream from step i) to simultaneously concentrate said liquid stream and remove inhibitory compounds by evaporation of volatile components, to obtain a concentrated liquid stream containing at most 6 g/L acetic acid, said evaporation being carried out at pressure and temperature conditions selected from the group consisting of: atmospheric pressure at a temperature of 90° C. to 100° C.; under vacuum of 50 mbar to 250 mbar at a temperature of 70° C. to 85° C., under pressure of 5 psig to 35 psig, and combinations thereof;
k) hydrolyzing xylooligosaccharides in said liquid stream from step i) before, during or after the concentrating step of step j);
l) hydrolyzing said cellulose rich solids stream from step i) with a mixture of cellulase and hemicellulose to obtain a hydrolyzed solid stream;
m) combining said hydrolyzed solids stream from step l) with said concentrated liquid stream to obtain a combined hydrolysate stream comprising hexose and pentose sugars;
n) co-fermenting said hexose and pentose sugars in said combined hydrolysate stream from step m) in a fermentation broth to produce ethanol;
o) distilling said ethanol from said fermentation broth from step n) to recover ethanol and a de-ethanolized slurry.

2. The process of claim 1, wherein said moisture content of said acidified biomass is adjusted in step e) to 65% to 80% prior to continuous steam treatment of step f).

3. The process of claim 1, wherein said moisture content of said acidified biomass is adjusted in step e) to 70% to 80% prior to continuous steam treatment.

4. The process of claim 1, wherein said mineral or organic acid is added to said squeezed biomass in step d) in an amount of 0.7% to 0.9% w/w.

5. The process of claim 1, wherein said mineral or organic acid is added to said squeezed biomass in step d) in an amount of 0.8% w/w.

6. The process of claim 1, wherein said biomass is steamed at atmospheric pressure for 10 to 60 min prior to subjecting said acidified biomass to steam treatment under pressure in a continuous treatment vessel.

7. The process of claim 1, further comprising the step of drying said de-ethanolized slurry.

8. The process of claim 7, further comprising the step of recovering energy produced from said pretreatment and drying steps.

9. The process of claim 1, wherein the amount of mineral acid added to said squeezed biomass in step d) is adjusted to achieve a pH of 1.8 to 2.5 in said acidified biomass.

10. The process of claim 9, wherein said acidified biomass is adjusted at a pH of 2.0.

11. The process of claim 9, wherein said mineral acid is selected from the group consisting of sulfuric acid, phosphoric acid, and sulfur dioxide.

12. The process of claim 1, wherein a severity index of the continuous steam treatment step f) is between 3.5 to 3.7.

13. The process of claim 12, wherein said severity index is between 3.5 to 3.6.

14. The process of claim 1, wherein extraction step i) comprises squeezing, water washing, or a combination thereof.

15. The process of claim 12 or 13, wherein extraction step i) is carried out at a pressure between atmospheric pressure and the pre-treatment pressure.

16. The process of claim 1, wherein said liquid stream extracted in step i) is concentrated in step j) by evaporation to a concentration of soluble solids between 100 to 300 g/L.

17. The process of claim 16, wherein energy required for the concentrating step j) is derived from recovered energy from the continuous steam treatment step f).

18. The process of claim 16, wherein vapors created in the concentrating step j) from said evaporation of the soluble solids are recovered.

19. The process of claim 1, wherein a consistency of said cellulose rich solids stream obtained in step i) is adjusted within a range of 10% to 25% consistency.

20. The process of claim 19, wherein said cellulose rich solids stream is adjusted to between 15% and 25% consistency.

21. The process of claim 19, wherein said cellulose rich solids stream is adjusted to 17% consistency.

22. The process of claim 1, wherein said combined hydrolysate stream is co-fermented to ethanol with bacteria or yeast that converts both glucose and xylose to ethanol.

23. The process of claim 7, wherein said drying of said de-ethanolized slurry takes place in a dryer for recovering heat as low pressure steam for use in other parts of the process.

24. The process of claim 1, wherein step j) is carried out at atmospheric pressure and a temperature of 98° C.

25. The process of claim 1, wherein step j) is carried out under a vacuum of 150 mbar and a temperature of 80° C.

26. The process of claim 1, wherein step j) is carried out at a pressure of 20 psig.

27. The process of claim 1, further comprising an extraction step, comprising squeezing, water washing or a combination thereof, prior to explosive decompression in step h).

* * * * *

UNITED STATES PATENT AND TRADEMARK OFFICE
CERTIFICATE OF CORRECTION

PATENT NO. : 9,434,961 B2  
APPLICATION NO. : 13/291659  
DATED : September 6, 2016  
INVENTOR(S) : Frank A. Dottori et al.

Page 1 of 1

It is certified that error appears in the above-identified patent and that said Letters Patent is hereby corrected as shown below:

In the Claims

Column 11, Claim 1, Line 27, delete "the" and insert therefor --a--;

Column 11, Claim 1, Line 35, delete "the";

Column 11, Claim 1, Line 37, delete "compounds" and insert therefor --compound--; and Column 12, Claim 10, Line 20, delete "at" and insert therefor --to--.

Signed and Sealed this  
Twenty-eighth Day of March, 2017

Michelle K. Lee  
*Director of the United States Patent and Trademark Office*